(12) United States Patent
Koob et al.

(10) Patent No.: US 10,653,514 B2
(45) Date of Patent: May 19, 2020

(54) COLLAGEN FIBER RIBBONS WITH INTEGRATED FIXATION SUTURES AND METHODS OF MAKING THE SAME

(71) Applicant: MiMedx Group, Inc., Marietta, GA (US)

(72) Inventors: Thomas J. Koob, Kennesaw, GA (US); Mengyan Li, Tampa, FL (US)

(73) Assignee: MiMedx Group, Inc., Marietta, GA (US)

( * ) Notice: Subject to any disclaimer, the term of this patent is extended or adjusted under 35 U.S.C. 154(b) by 381 days.

(21) Appl. No.: 15/466,299

(22) Filed: Mar. 22, 2017

(65) Prior Publication Data

US 2017/0189163 A1 Jul. 6, 2017

Related U.S. Application Data

(62) Division of application No. 14/003,484, filed as application No. PCT/US2012/027366 on Mar. 2, 2012, now Pat. No. 9,636,209.

(Continued)

(51) Int. Cl.
| | |
|---|---|
| *A61F 2/08* | (2006.01) |
| *A61L 17/08* | (2006.01) |
| *D01F 4/00* | (2006.01) |
| *D04C 1/12* | (2006.01) |
| *D03D 3/00* | (2006.01) |
| *D03D 15/00* | (2006.01) |
| *A61B 17/06* | (2006.01) |
| *D04C 3/00* | (2006.01) |
| *A61B 17/00* | (2006.01) |

(52) U.S. Cl.
CPC .......... *A61F 2/08* (2013.01); *A61B 17/06166* (2013.01); *A61L 17/08* (2013.01); *D01F 4/00* (2013.01); *D03D 3/005* (2013.01); *D03D 15/00* (2013.01); *D04C 1/12* (2013.01); *D04C 3/00* (2013.01); *A61B 2017/00867* (2013.01); *A61B 2017/00893* (2013.01); *A61B 2017/00964* (2013.01); *D10B 2403/0311* (2013.01); *D10B 2509/04* (2013.01); *F04C 2270/0421* (2013.01)

(58) Field of Classification Search
CPC .................................................. D10B 2211/06
See application file for complete search history.

(56) References Cited

U.S. PATENT DOCUMENTS

| 3,316,699 A | 5/1967 | Mattingly |
|---|---|---|
| 4,590,928 A | 5/1986 | Hunt et al. |
| | (Continued) | |

FOREIGN PATENT DOCUMENTS

| CA | 2285161 | 5/1996 |
|---|---|---|
| EP | 1493404 | 1/2005 |
| | (Continued) | |

OTHER PUBLICATIONS

Becker et al. "Early active motion following a beveled technique of flexor tendon repair: Report on fifty cases" *Journal of Hand Surgery*, 1979, vol. 4 No. 5, pp. 454-460.

(Continued)

*Primary Examiner* — Megan Y Wolf
(74) *Attorney, Agent, or Firm* — Myers Bigel, P.A.

(57) ABSTRACT

The disclosure describes implantable bioprosthesis and constructs having an implantable woven ribbon with at least one integrated suture.

26 Claims, 7 Drawing Sheets

Related U.S. Application Data

(60) Provisional application No. 61/450,179, filed on Mar. 8, 2011.

(56) References Cited

U.S. PATENT DOCUMENTS

| | | | |
|---|---|---|---|
| 4,792,336 | A | 12/1988 | Hlavacek et al. |
| 4,839,215 | A | 6/1989 | Starling et al. |
| 4,841,962 | A | 6/1989 | Berg et al. |
| 4,883,486 | A | 11/1989 | Kapadia et al. |
| 4,979,956 | A | 12/1990 | Silvestrini |
| 5,078,744 | A | 1/1992 | Chvapil |
| 5,106,949 | A | 4/1992 | Kemp et al. |
| 5,256,418 | A | 10/1993 | Kemp et al. |
| 5,263,984 | A | 11/1993 | Li et al. |
| 5,378,469 | A | 1/1995 | Kemp et al. |
| 5,656,605 | A | 8/1997 | Hansson et al. |
| 5,713,374 | A | 2/1998 | Pachence et al. |
| 5,718,012 | A | 2/1998 | Cavallaro |
| 5,718,717 | A | 2/1998 | Bonutti |
| 6,090,117 | A | 7/2000 | Shimizu |
| 6,224,630 | B1 | 5/2001 | Bao et al. |
| 6,277,397 | B1 | 8/2001 | Shimizu |
| 6,280,474 | B1 | 8/2001 | Cassidy et al. |
| 6,292,697 | B1 | 9/2001 | Roberts |
| 6,335,007 | B1 | 1/2002 | Shimizu et al. |
| 6,531,147 | B2 | 3/2003 | Sawhney et al. |
| 6,565,960 | B2 | 5/2003 | Koob et al. |
| 6,589,257 | B1 | 7/2003 | Shimizu |
| 6,592,623 | B1 | 7/2003 | Bowlin et al. |
| 6,645,247 | B2 | 11/2003 | Ferree |
| 6,692,528 | B2 | 2/2004 | Ward et al. |
| 6,713,537 | B1 | 3/2004 | Ueda et al. |
| 6,716,234 | B2 | 4/2004 | Grafton et al. |
| 6,730,124 | B2 | 5/2004 | Steiner |
| 6,752,831 | B2 | 6/2004 | Sybert et al. |
| 6,821,530 | B2 | 11/2004 | Koob et al. |
| 6,936,072 | B2 | 8/2005 | Lambrecht et al. |
| 6,955,683 | B2 | 10/2005 | Bonutti |
| 7,084,082 | B1 | 8/2006 | Shimizu |
| 7,090,690 | B2 | 8/2006 | Foerster et al. |
| 7,115,146 | B2 | 10/2006 | Boyer et al. |
| 7,135,040 | B2 | 11/2006 | Wang et al. |
| 7,309,359 | B2 | 12/2007 | Trieu et al. |
| 7,354,627 | B2 | 4/2008 | Pedrozo et al. |
| 8,100,942 | B1 | 1/2012 | Green et al. |
| 2001/0018619 | A1 | 8/2001 | Enzerink et al. |
| 2002/0037940 | A1 | 3/2002 | Koob et al. |
| 2002/0095218 | A1 | 7/2002 | Carr, Jr. et al. |
| 2002/0103503 | A1 | 8/2002 | Torgerson et al. |
| 2002/0123805 | A1 | 8/2002 | Murray et al. |
| 2003/0100108 | A1 | 5/2003 | Altman et al. |
| 2003/0230316 | A1 | 12/2003 | Glucksman et al. |
| 2004/0110439 | A1 | 6/2004 | Chaikof et al. |
| 2004/0131562 | A1 | 7/2004 | Gower et al. |
| 2004/0193241 | A1 | 9/2004 | Stinson |
| 2004/0224406 | A1 | 11/2004 | Altman et al. |
| 2004/0267362 | A1 | 12/2004 | Hwang et al. |
| 2005/0027307 | A1 | 2/2005 | Schwartz et al. |
| 2005/0033362 | A1 | 2/2005 | Grafton |
| 2005/0192631 | A1 | 9/2005 | Grafton |
| 2006/0095134 | A1 | 5/2006 | Trieu et al. |
| 2006/0167561 | A1 | 7/2006 | Odar et al. |
| 2006/0257377 | A1 | 11/2006 | Atala et al. |
| 2006/0263417 | A1 | 11/2006 | Lelkes et al. |
| 2007/0118217 | A1 | 5/2007 | Brulez et al. |
| 2007/0248643 | A1 | 10/2007 | Devore et al. |
| 2008/0020012 | A1 | 1/2008 | Ju et al. |
| 2008/0038352 | A1 | 2/2008 | Simpson et al. |
| 2008/0051834 | A1 | 2/2008 | Mazzocca et al. |
| 2008/0124371 | A1 | 5/2008 | Turos et al. |
| 2008/0161917 | A1 | 7/2008 | Koob et al. |
| 2008/0188933 | A1 | 8/2008 | Koob et al. |
| 2008/0200992 | A1 | 8/2008 | Koob et al. |
| 2008/0215150 | A1 | 9/2008 | Koob et al. |
| 2009/0105753 | A1 | 4/2009 | Greenhalgh et al. |
| 2009/0216233 | A1 | 8/2009 | Wiedrich et al. |
| 2009/0222039 | A1 | 9/2009 | Dreyfuss et al. |
| 2009/0228021 | A1* | 9/2009 | Leung ............ A61B 17/06166 606/139 |
| 2009/0287308 | A1 | 11/2009 | Davis et al. |
| 2011/0054524 | A1 | 3/2011 | Beevers et al. |
| 2011/0282448 | A1 | 11/2011 | Paulos et al. |

FOREIGN PATENT DOCUMENTS

| | | |
|---|---|---|
| WO | WO 93/06791 | 4/1993 |
| WO | WO 95/25482 | 9/1995 |
| WO | WO 96/14095 | 5/1996 |
| WO | WO 2001/072241 | 10/2001 |
| WO | WO 2008/041183 | 4/2008 |

OTHER PUBLICATIONS

Biosingularity, Advances in biological systems, Google Ad, MIT Technology Review, 2006, 1 Page.

Brunelli et al. "Slip-knot flexor tendon suture in zone II allowing immediate mobilisation" *The Hand* 1983, vol. 15, pp. 352-358.

Conair QB3ECS Quick Braid Styling Kit, *Product advertisement* © 2007 (1 page).

FiberWire® Braided Composite Suture, Arthrexe, Product Brochure, 10 pages, © Copyright Arthrex Inc., 2005, Date unknown but believed to be prior to the priority date of the present application.

Greis et al. "The influence of tendon length and fit on the strength of the tendon-bone tunnel complex" *Am. J. Sports Med.*, 2001, 29:493-497.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Integra™ NeuraGen™ Nerve Guide, Product Broacher, 4 pages (2005).

Integra™ NeuraGen™ Nerve Guide, Product Webpage, http://www.integra-ls.com/products/?product=88, Date unknown but believed to be prior to the filed of the present application, 2 pages.

Integra™ NeuraWrap™ Nerve Protector, Product Webpage, http://www.integra-ls.com/products/?product=198, Date unknown but believed to be prior to the filed of the present application, 2 pages.

International Search Report and the Written Opinion of the International Searching Authority corresponding to International Patent Application No. PCT/US2012/027366 (dated Sep. 27, 2012).

Kakisis, J., et al., Artificial blood vessel: The Holy Grail of peripheral vascular surgery, Journal of Vascular Surgery, vol. 41, Issue 2, 2003, pp. 349-354 (abstract only).

Koob et al. "Biocompatibility of NDGA-polymerized collagen fibers. I. Evaluation of cytotoxicity with tendon fibroblasts in vitro" © 2001John Wiley & Sons, Inc.

Koob et al. "Biocompatibility of NDGA-polymerized collagen fibers. II. Attachment, proliferation, and migration of tendon fibroblasts in vitro" © 2001John Wiley & Sons, Inc.

Koob et al. "Biomimetic approaches to tendon repair" *Comp. Biochem. Physiol. A Mol. Integr. Phys.*, 2002, 133: 1171-1192.

Koob et al. "Material properties of NDGA-collagen composite fibers: development of biologically based tendon constructs" *Biomaterials*, 2002, 23:202-212.

Koob et al. "Mechanical and thermal properties of novel polymerized NDGA-gelatin hydrogels" *Biomaterials*, 2002, 24:1285-1292.

Martin et al. "Anterior Cruciate Ligament Graft Preparation: A New and Quick Alternative to the Whipstitch" *Arthroscopy: The Journal of Arthroscopic & Related Surgery*, Online Publication Date of Nov. 29, 2006.

Messina "The double armed suture: Tendon repair with immediate mobilization of the fingers" *Journal of Hand Surgery*, 1992, 17A:137-142.

Nottage et al. "Arthroscopic Knot Tying Techniques" *Arthroscopy: The Journal of Arthroscopic & Related Surgery* 15(1999): 515-521.

Powell et al. "Forces transmitted along human flexor tendons during passive and active movements of the fingers" *J. Hand Surg.*, 2004, 29:4:386-389.

(56) References Cited

OTHER PUBLICATIONS

Rodeo et al. "Tendon healing in a bone tunnel. A biomechanical and histological study in a dog" *J. Bone Joint Surg.*, 1993, 75:1795-1803.
Savage et al. "Flexor tendon repair using a "six strand" method of repair and early active mobilisation" *Journal of Hand Surgery*, (British vol. 1989), 14B:396-399.
Silva et al. "The insertion site of the canine flexor digitorum profundus tendon heals slowly following injury and suture repair" *J. Orthop. Res.*, 2002, 20:447-453.
Supplementary Partial European Search Report for corresponding EP Application No. EP12755493.9, 8 pages (dated Jan. 16, 2015).
Trotter et al. "Molecular structure and functional morphology of echinoderm collagen fibrils" *Cell Tiss. Res.*, 1994, 275: 451-458.

\* cited by examiner

COLLAGEN FIBER RIBBONS WITH INTEGRATED FIXATION SUTURES AND METHODS OF MAKING THE SAME

RELATED APPLICATIONS

This application is a divisional of U.S. patent application Ser. No. 14/003,484, filed Mar. 5, 2014, which is a 35 USC § 371 national phase application of PCT/US2012/027366, International Filing Date Mar. 2, 2012, which claims the benefit of and priority to U.S. Provisional Application Ser. No. 61/450,179 filed Mar. 8, 2011, the contents of which are hereby incorporated by reference as if recited in full herein.

FIELD OF THE INVENTION

The invention relates to medical ribbons.

BACKGROUND OF THE INVENTION

It is believed that the linear organization of natural collagen fibers in tendons results in optimal stiffness and strength at low strains under tensile loads. However, this organization makes repairing ruptured or lacerated tendons difficult. Current suturing techniques to join split ends of tendons, while providing sufficient mechanical strength to prevent gapping, are often inadequate to carry normal loads and may not ever allow the tendon to regain original mechanical properties or mobility. Immobilization protocols used to restore tendon congruity may result in scar formation at the repair site and peripheral adhesions that can limit excursions. One or more similar issues may be associated with conventional ligament repair techniques.

SUMMARY OF EMBODIMENTS OF THE INVENTION

Embodiments of the invention are directed to medical ribbons. The ribbons include a woven ribbon body of a plurality of synthetic warp and weft collagen fiber yarns. The ribbon body has opposing first and second end portions spaced apart in a length dimension connected by transversely spaced apart first and second long sides defining a width dimension.

The ribbon body can optionally include at least one suture woven into the ribbon body and oriented to extend in a substantially straight linear orientation along the length of the ribbon body. The at least one suture can extend a length beyond both end portions of the ribbon body.

The ribbon body can optionally include some collagen fibers cross-linked with a first agent and some collagen fibers cross-linked with a second (different) agent to provide the respective fibers or yarns formed using those fibers with respective different mechanical properties and/or degradation rate.

In some embodiments, the at least one suture is held only under weft yarns so that the at least one suture is visible on a first primary surface of the ribbon body.

In some embodiments, the weft yarns crossover the at least one suture once about every 1 mm to about every 1 inch along the length of the ribbon body.

The weft yarns can crossover the suture in a regular repeating pattern over at least a major The at least one suture can be defined by a plurality of long collagen fiber warp yarns that have a length that is at least about 50% longer than other collagen fiber warp yarns of the ribbon body. The tails of the long collagen fiber warp yarns can be braided together outside the ribbon body.

The at least one suture can be a single suture that is attached to the ribbon body proximate a longitudinally extending centerline of the ribbon body.

The at least one suture can be a plurality of sutures, at least one of which extends proximate each long side of the ribbon body.

The at least one suture can be four separate sutures, two each attached to a respective long side of the ribbon body.

The synthetic collagen fibers comprise NDGA polymerized collagen fibers.

In some embodiments, some of the yarns comprise collagen fibers cross-linked with NDGA and other yarns comprise collagen fibers cross-linked with a different agent. For example, some of the yarns comprise fibers cross-linked with NDGA and fibers cross-linked with a different agent.

The ribbon can have a greater number of warp yarns than weft yarns.

The at least one suture can include a suture comprising at least one NDGA treated collagen fiber.

The at least one suture can be defined by four NDGA treated collagen fiber sutures, two each attached to a respective long side of the ribbon body and the synthetic collagen fibers can include NDGA polymerized collagen fibers.

The different agent can be EDC and the EDC collagen fibers degrade faster than the NDGA collagen fibers.

The at least one suture can be defined by a plurality of NDGA treated collagen fiber yarns that define warp yarns along a length of the ribbon body and have a length sufficient to extend outwardly therefrom to define tail segments that have a length of between about 2 inches to about 15 inches.

Still other embodiments are directed to methods of making a medical ribbon, including: (a) providing a plurality of discrete continuous length synthetic collagen fibers; (b) braiding the fibers into yarns; (c) providing at least one suture; and (d) weaving the collagen fiber yarns together to form a ribbon body with a length while crossing weft yarns over a top of the suture at intervals along the length of the ribbon to attach the at least one suture to the woven ribbon body and define at least one tail extension with a length of at least about 1 inch that extends off at least one end of the ribbon body.

The weaving step can be carried out by attaching a single suture to the ribbon body so that the single suture resides in a substantially straight line proximate a longitudinally extending centerline of the ribbon body.

The providing step can be carried out to provide a plurality of sutures. The weaving step can be carried out to attach the plurality of sutures to the ribbon body so that at least one suture resides in a substantially straight line proximate one long side of the ribbon body and at least one suture resides in a substantially straight line proximate the other long side of the ribbon body.

The plurality of sutures can be four sutures, two on each respective long side of the ribbon body.

The weaving step can be carried out to have the weft yarns hold the suture at discrete repeating segments along the length of the ribbon body.

The synthetic fibers can include NDGA polymerized collagen fibers.

Some of the collagen fibers can be cross-linked with a first agent and some of the collagen fibers can be cross-linked with a different cross-linking agent to provide a different fiber tensile strength and a different intrabody degradation rate.

The at least one suture can be defined by a plurality of long warp collagen fiber yarns with a length that is at least about 50% greater than other (shorter) warp collagen fiber yarns in the ribbon body. The longer yarns can be woven medially proximate a longitudinally extending centerline of the ribbon body to define two opposing tail ends.

Still other embodiments are directed to methods of making a medical ribbon, that include: (a) providing a plurality of collagen fiber warp yarns having a first length, each yarn comprising a plurality of synthetic collagen fibers; (b) providing a plurality of long collagen fiber warp yarns having a second length that is at least about 50% longer than the warp yarns first length, each long yarn comprising a plurality of synthetic collagen fibers; (b) providing a plurality of collagen fiber weft yarns, each yarn comprising a plurality of synthetic collagen fibers; and (c) weaving the collagen fiber weft and warp yarns together to from a ribbon body using the long collagen fiber warp yarns to define tails that extend beyond both ends of the ribbon body a distance of at least about 1 inch off at least one end of the ribbon body.

The weaving step may be carried out using the long warp yarns as substantially central warp yarns with warp yarns of the first (shorter) length on both sides thereof. The method may include braiding the tails of the long warp yarns.

Still other methods are directed to repairing soft tissue. The methods include: (a) placing a ribbon comprising synthetic collagen fibers and at least one integrated suture either: (i) held only by weft yarns of the ribbon over a length of the ribbon or (ii) defined by longer collagen warp fibers of the ribbon, such that lengths of the at least one suture extend a distance beyond each end of the ribbon in a patient's body; and (b) attaching the at least one suture to local structure to affix the ribbon in a desired position in the patient's body thereby repairing soft tissue in the patient's body.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Further features, advantages and details of the present invention will be appreciated by those of ordinary skill in the art from a reading of the figures and the detailed description of the embodiments that follow, such description being merely illustrative of the present invention.

DETAILED DESCRIPTION

Figure 1:
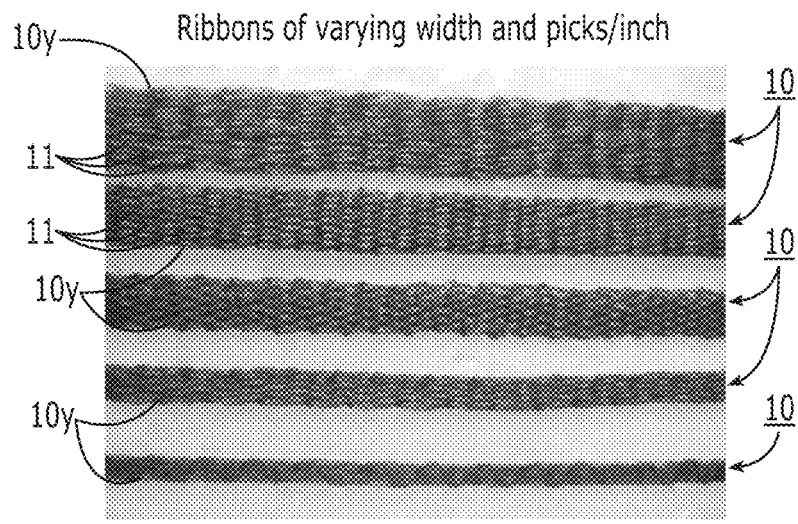
FIG. 1 is a digital photograph of examples of ribbons of varying widths and picks/inch (cross-over) of fibers used to form the medical ribbons according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" and "construct" are used interchangeably herein to designate an implantable product configured to repair, replace or supplement tissue such as at least a portion of a natural tendon, ligament, nerve, or other tissue of a mammalian subject (for veterinary or medical (human) applications). The term "implantable" means the device can be inserted, embedded, grafted or otherwise chronically attached or placed on or in a patient.

The term "about" means that the recited number can be more or less than the actual number, typically by about +/−20%, and more typically by about +/−10%, of the respective number.

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic (collagen) fiber but a tendon fiber newly harvested from a mammal is a natural fiber. Of course, synthetic collagen fibers can include non-collagenous components, such as particulates, hydroxyapatite and other mineral phases, or drugs that facilitate tissue growth. See, U.S. Pat. No. 6,821,530, hereby incorporated by reference herein. For example, the compositions can contain carbon nano-tubes, zinc nano-wires, nano-crystalline diamond, or other nano-scale particulates; larger crystalline and non-crystalline particulates such as calcium phosphate, calcium sulfate, apatite minerals. For example, the fibers and/or constructs formed of the fibers can include compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. In some embodiments, the fibers and/or constructs can contain cells, engineered cells, stem cells, and the like, as well as combinations of the above.

The term "suture" refers to an elongate material that is used to attach a ribbon to a target anatomical structure to help hold the ribbon in location in or on the body. The suture may be resorbable or non-resorbable, synthetic or natural. The suture can be configured to hold the implant in location for at least an initial post-implantation period of at least about 1 week, but may reside permanently in the body or, as noted above, may be substantially resorbable over time. The suture can be a single filament or multi-filament (braided or unbraided) thread, floss, gut or wire, or combinations thereof that can be used to hold a portion of an implant against or attached to target structures, typically to bone and/or tissue. The suture may comprise a resorbable or non-resorbable biocompatible material. Examples of suture materials include chromic gut (an absorbable, sterile surgical suture composed of purified connective tissue (mostly collagen)) derived from intestines, e.g., either the serosal layer of bovine or the submucosal fibrous layer of ovine intestines, cross-linked collagen fibers, polymeric materials including, for example, polyester and nylon, elastomeric materials, such as, for example, polymers, copolymers and/or derivatives thereof, including Vicryl®, as well as other materials including, for example, NITINOL, braided composite sutures including sutures with a multi-strand long chain polyethylene core and a polyester braided jacket such as FiberWire® and combinations thereof. The suture may optionally be used with a suture anchor (bone or tissue anchor).

The term "flexible" means that the so-called member can be flexed or bent.

The term "woven" and derivatives thereof means a product that is formed using warp and weft fibers woven in a manner that provides desired mechanical properties for a particular application (e.g., rotator cuff repair or ACL repair). The warp threads run lengthways of the piece of cloth, and the weft runs across from side to side. The term "ribbon" refers to a substantially flat woven medical construct that is particularly suitable for soft-tissue repair.

Optionally, it is also contemplated that, in some particular embodiments, the ribbons may be used as an external covering such as a scaffold to promote skin growth or an internal covering of an implantable device such as a pacemaker. In some embodiments, the ribbon can be used to help re-attach bone pieces such as a separated sternum or bone fractures.

FIG. 1 shows exemplary ribbons 10 of different widths and braid patterns. The ribbons 10 can have any suitable number of yarns 10y, any suitable number of fibers 11 in each yarn, and/or any desired number of picks/inch to form the braid pattern. In some embodiments, the ribbons 10 can have a substantially repeating weft pattern with a weft yarn(s) having a cross-over (a frequency) of about every 0.1 mm to about every 25 mm, typically between about every 0.5-10 mm, and more typically in a substantially repeating pattern with a cross over between about every 1-5 mm.

Each yarn 10y in a ribbon 10 can be a single fiber (also known as filament) yarn or multi-fiber (multi-filament) yarn. Some yarns 10y may have more fibers than others in a respective ribbon 10 or all the yarns may have the same number of fibers 11. The fiber 11 or fibers in each yarn(s) 10y may be twisted or untwisted, or combinations of twisted and untwisted may be used for each or respective different yarns within a single ribbon 10.

In some embodiments, the ribbons have a lesser number of weft yarns compared to warp yarns and can be configured to provide a low-profile relatively smooth ribbon body. The ribbons can have suitable warp density, weft density, ribbon count, ribbon weights and the like for different uses.

In some embodiments, the yarns 10y can each have between about 1-100 elongate continuous length collagen fibers (treated to improve strength, such as treated with NDGA), typically between about 5-20 fibers in each yarn 10y. That is, the collagen fibers 11 can have a length sufficient to extend over substantially the entire length of the ribbon body. The ribbons 10 may have between about 1-1000 yarns, typically between about 3-100 yarns some of which are weft and some of which are warp yarns. For example, the ribbon body 10b can include between about 10-100 warp yarns 10y of between about four to eight long NDGA treated collagen fibers 11 may be twisted or braided together for a respective yarn. The ribbon 10 shown in FIG. 2B illustrates 10 yarns of eight fibers each. The ribbon 10 shown in FIG. 11 includes 40 warp yarns; 8 braided fibers per yarn.

The ribbons 10 can be configured to have substantially the same physical thickness and/or configuration as the replaced or repaired tissue so as to not cause discomfort or physical abnormalities in structure.

As desired, the body of the ribbon 10 can include a smooth outer sheath that may be formed by a coating, gel or other material. In particular embodiments, the ribbon 10 can comprise polyglycolic acid, polylactic acid, or combinations of these or other substances.

In some embodiments, the ribbon 10 can have a length that is between about 0.5-50 cm, typically between about 1-25 cm, and in some embodiments between about 2 cm to about 20 cm long. The ribbon 10 may have a width between about 0.05 to 8 cm, and is typically between about 1-3 cm. The ribbon 10 may have a thickness of between about 0.01 to about 30 mm, typically about 1-10 mm. The at least one suture 20 can extend at least about 1 inch off beyond each end of the ribbon body, typically between about 1-15 inches. The suture(s) 20 can be shorter on one end than the other (not shown).

The at least one suture 20 can be held only under weft yarns 10y so that the at least one suture is visible on a first primary (e.g., upper or lower flat) surface of the ribbon body 10b. The weft yarns can cross over the at least one suture 20 as discussed above, such as, for example, once about every 1 mm to about once every 1 inch along the length of the ribbon body. The weft yarns 10y can crossover the suture 20 in a regular repeating pattern over at least a major portion of the length of the ribbon body.

Figure 2A:
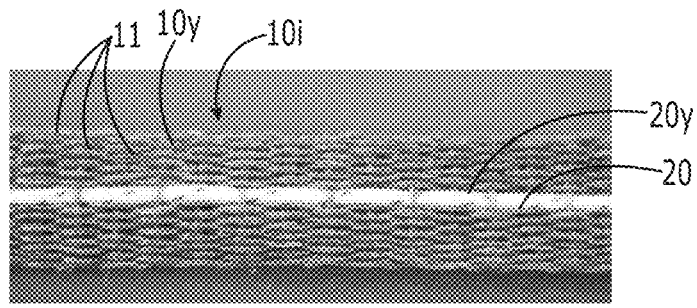
FIG. 2A is a digital photograph of a portion of a ribbon with an integrated suture according to embodiments of the present invention.
Figure 2B:
FIG. 2B is a digital photograph of a portion of a narrower ribbon with an integrated suture similar relative to the ribbon shown in FIG. 2A according to embodiments of the present invention.
Figure 3:
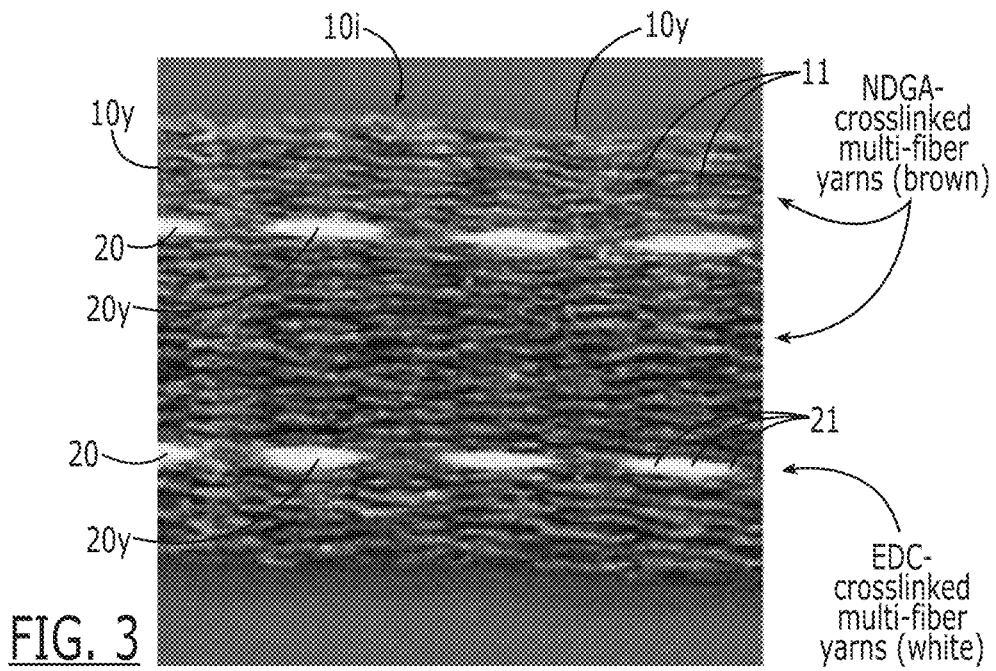
FIG. 3 is an enlarged digital photograph of a ribbon with a plurality of integrated sutures according to embodiments of the present invention.

FIGS. 2A, 2B and 3 illustrate examples of ribbons 10i with at least one integrated suture 20 that extends beyond at least one end of the ribbon body 10b, and typically beyond both ends of the ribbon body 10b a distance of at least about 1 inch. The at least one suture 20 can be woven into the weave of the ribbon body without requiring any supplemental fixation members providing for a seamless smooth configuration. FIGS. 2A and 2B illustrate a single (multi-fiber) suture 20 that is woven into an axially extending (lengthwise direction) center portion of the ribbon body 10 and extends substantially straight throughout the length of the ribbon body. Two or more (typically substantially) parallel sutures oriented to extend in the lengthwise direction may also be used instead of the single suture shown.

FIG. 3 illustrates that the ribbon 10i can have at least two transversely spaced apart sutures 20 that extend continuously and substantially equally spaced from an outer edge of respective long sides of the ribbon 10i over the entire length of the ribbon body 10b. Two or more substantially parallel sutures (one above the other) for each of the spaced apart sutures may also be used instead of the single suture shown.

The suture 20 can comprise one or more suture yarns 20y of a single fiber 21 or multiple fibers 21, typically multiple synthetic collagen fibers 21, such as between about 2-100 elongate collagen fibers in a respective yarn 20y. The suture yarn 20y can be provided as twisted and/or braided fibers, or snugly held sets of parallel fibers or yarns and/or sets of yarns 20y.

FIG. 3 illustrates that the ribbon body 10b of the integrated ribbon 10i can comprise two different types of collagen fibers, each cross-linked with a different chemical providing different mechanical properties such as tensile strength and/or degradation or resorption properties. The suture yarn(s) 20y can have a greater number of fibers than the ribbon yarns 10y, typically at least about 50% more. The ribbons 10i can include NDGA-cross linked multi-collagen fiber yarns 10y (e.g., 8 fiber braided yarns) forming the ribbon body, shown as the darker colored fibers. The suture yarns 20y can comprise 1-ethyl-3-(3-dimethylaminopropyl)-carbodiimide (EDC) cross linked multi-collagen fiber yarns, shown as the lighter color fibers (e.g., 16-fiber braided yarns). The number of fibers in each yarn 10y can vary depending on the target end use, typically between about 1-100 as noted above. In some embodiments at least some of the yarns 10y in a particular ribbon body 10b can have between about 2-50 continuous length collagen fibers, such as any number therebetween, including 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Figure 4A:
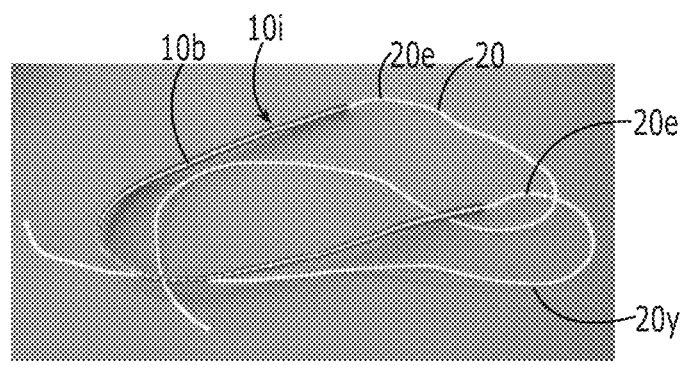
FIG. 4A is a digital photograph of a narrow ribbon with an integrated suture according to yet other embodiments of the present invention.
Figure 4B:
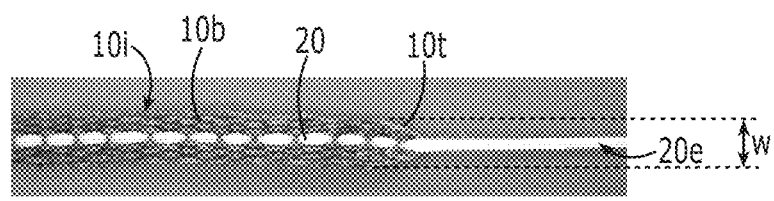
FIG. 4B is an enlarged close-up view of a portion of the narrow ribbon shown in FIG. 4A according to embodiments of the present invention.

FIG. 4A illustrates another example of a ribbon 10i with an integrated suture 20. In this embodiment, the ribbon body 10b is relatively narrow, and can have a width "W" that is less than about five (5) times the size of the suture 20. The suture 20 can be woven into the ribbon body 10b and extend axially over the entire ribbon body and extend a distance on each end outside the ribbon body. The extension lengths 20e can be at least about 30% of the length of the ribbon body, and in some embodiments may be about the same or greater than the length of the ribbon body. FIG. 4B is a greatly enlarged view of one end of the ribbon 10i showing that the ribbon body may include a taper 10t so that the body tapers slightly inward to form a narrower portion proximate the extension segment 20e of the suture. The taper 10t can be the result of the weave pattern and does not require any physical gluing or stitching at this junction. In other embodiments, the taper can be held in its shape using a biocompatible adhesive. This weave attachment can provide a smooth and seamless configuration of the suture 20 and ribbon body 10b. This configuration may be particularly suitable for rotator cuff repairs.

Figure 5A:
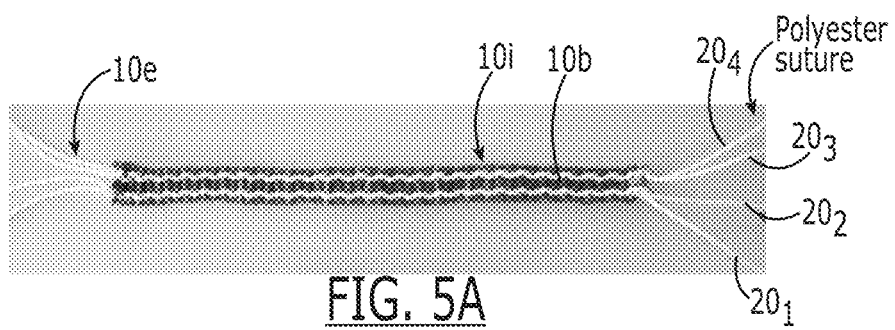
FIGS. 5A and 5B are digital photographs of ribbons with pairs of integrated sutures on each long side of the ribbon according to embodiments of the present invention.
Figure 5B:
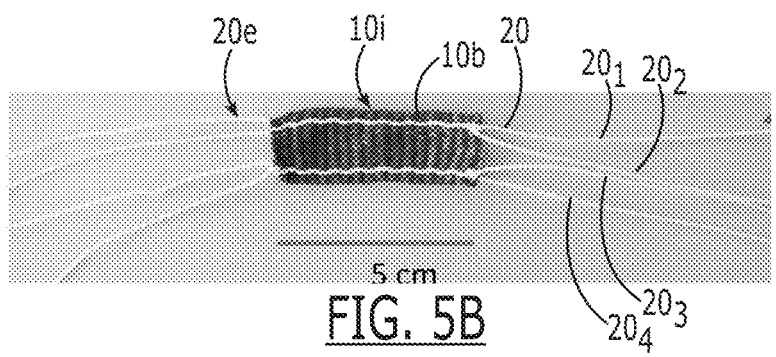
Figure 6A:
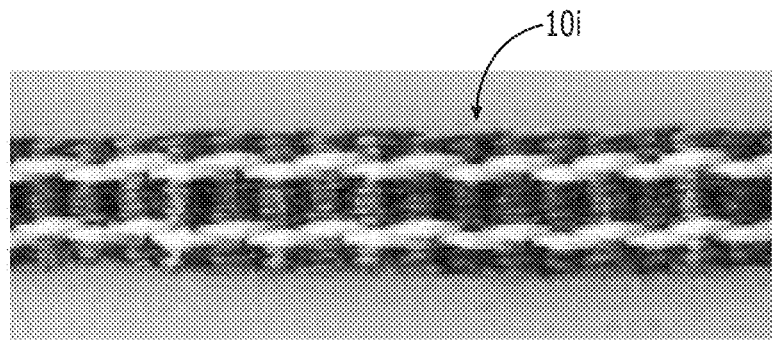
FIG. 6A is an enlarged view of a portion of the ribbon shown in FIG. 5A.
Figure 6B:
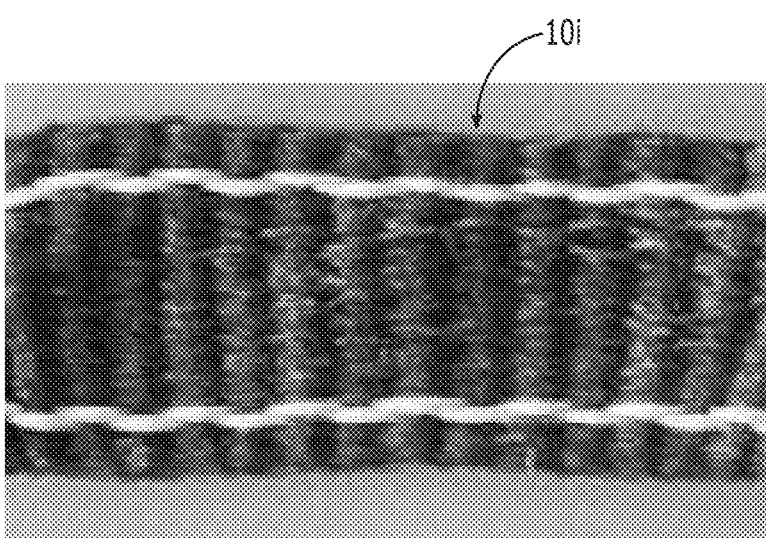
FIG. 6B is an enlarged view of a portion of the ribbon shown in FIG. 5B.

FIGS. 5A and 5B illustrate examples of ribbons 10i with transversely spaced apart pairs of sutures $20_1$, $20_2$ and $20_3$, $20_4$ woven directly into the ribbon body 10b, one pair proximate each opposing outer long side of the ribbon body 10b. FIG. 6A is an enlarged view of a portion of the relatively long and more narrow ribbon 10i shown in FIG. 5A, and FIG. 6B is an enlarged view of a portion of the relatively wide and shorter ribbon 10i shown in FIG. 5B (e.g., typically about 5 cm long and about 1 to about 2 cm across or wide).

Figure 7A:
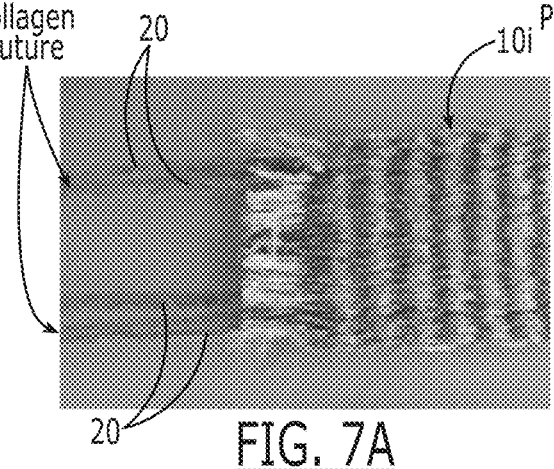
FIGS. 7A and 7B are view of end portions of ribbons similar to those shown in FIGS. 5A and 5B with different suture types according to embodiments of the present invention.
Figure 7B:
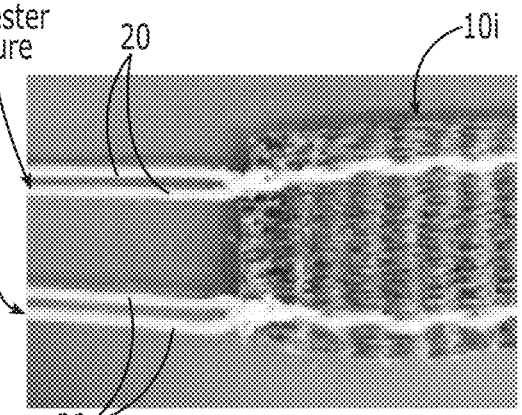

FIGS. 7A and 7B illustrate two different suture materials for pairs of sutures (such as described above with respect to FIGS. 5A and 5B). FIG. 7A illustrates that the sutures 20 can be continuous length NDGA treated collagen fibers while FIG. 7B illustrates polyester sutures.

FIG. 7A also illustrates that the sutures 20 do not appear on one primary surface of the ribbon body. This is because the ribbon 10i can be woven over a top of the suture(s) 20. This suture integration feature can be true for all the embodiments discussed or shown herein.

Figure 8A:
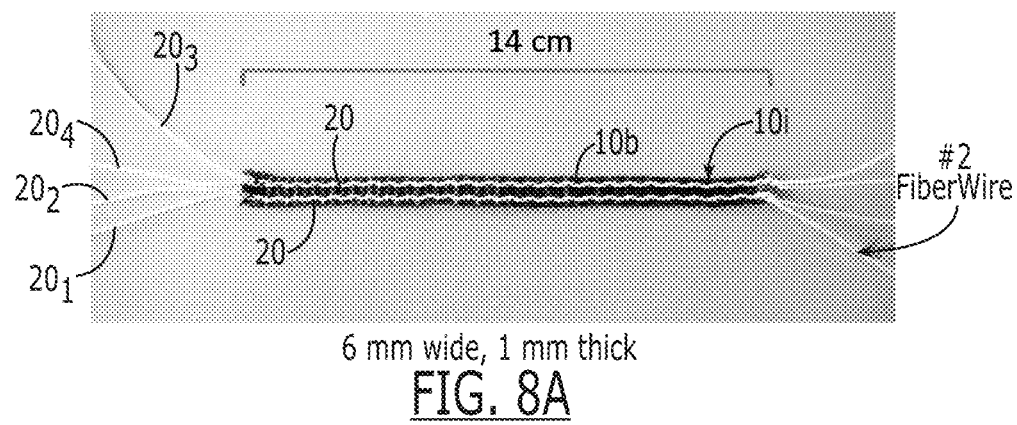
FIG. 8A is a digital photograph of ribbon with four independent integrated sutures of #2 FiberWire® suture according to embodiments of the present invention.
Figure 8B:
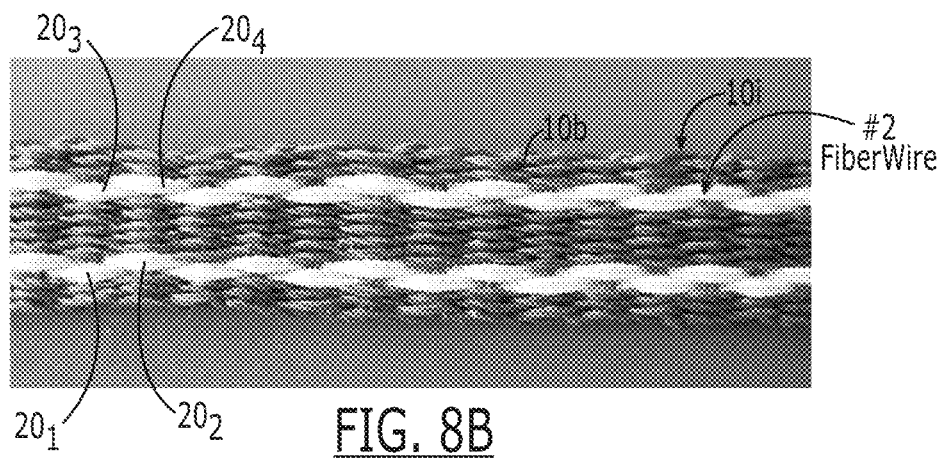
FIG. 8B is an enlarged view of the ribbon shown in FIG. 8A.
Figure 9A:
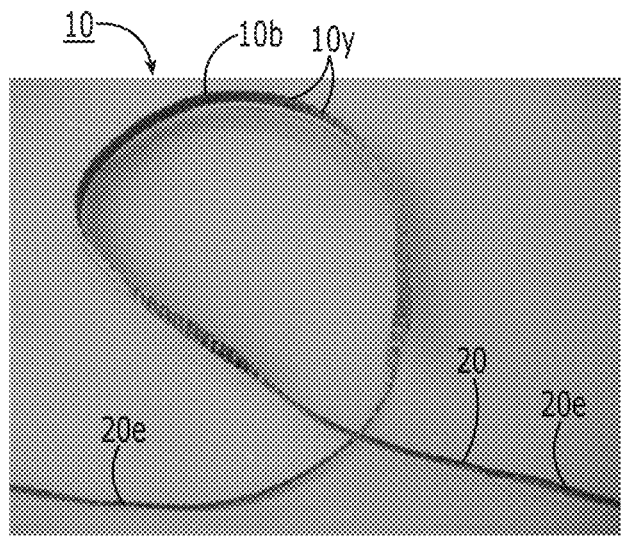
FIGS. 9A-9D are digital photographs of an exemplary narrow ribbon according to embodiments of the present invention.
Figure 9B:
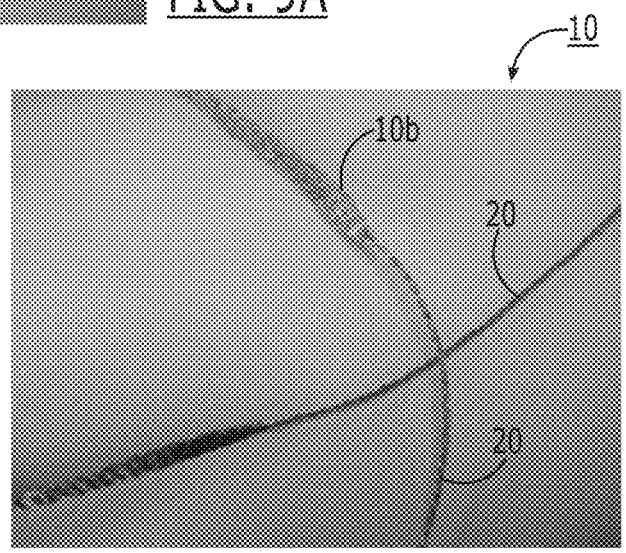
Figure 9C:
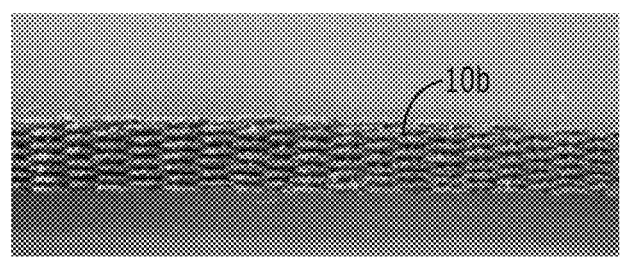
Figure 9D:
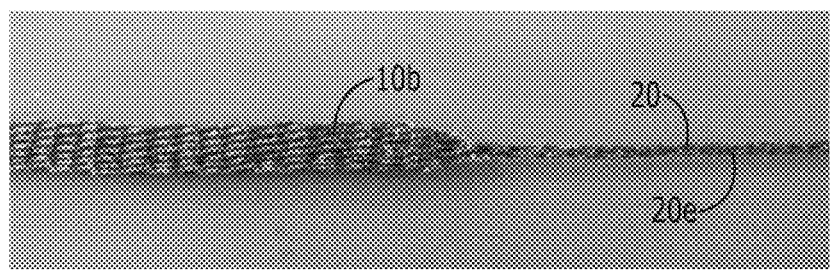

FIGS. 8A and 8B illustrate an embodiment similar to that shown in FIGS. 5A and 6A. As shown, the ribbon 10i has four independent or separate sutures, typically two adjacent sutures proximate a respective outer long side edge of the ribbon body. The sutures $20_1$, $20_2$ and $20_3$, $20_4$ are woven to the ribbon body 10b which, as shown, can have a relatively tight weave pattern. The ribbon body 10b can be between about 3-8 mm wide, about 1 mm thick, and about 5-30 cm long. The cooperating pairs of sutures can be used to affix the ribbon to local structure and may provide a more balanced fixation (torque resistant).

In some embodiments, the ribbon bodies 10b and/or sutures 20 can be configured to have benign degradation. The term "benign degradation" means that the component degrades in the body without producing adverse or unnatural effects. For example, PLA sutures when degrading can produce an acidic environment. The sutures 20 can consist essentially of synthetic collagen fibers that produce no such adverse effects.

In some embodiments, the ribbon bodies 10b can be configured with tunable degradation. The term "tunable degradation" means that different parts degrade in the body at different rates (e.g., break down at different times). The word "tuning" refers to the fact that the ribbon composition and/or fibers can be configured in a custom manner so that degradation can be specifically designed for different uses/sites. The tunable degradation can be provided by cross-linking different collagen fibers with different agents. For example, some collagen fibers 11 can be cross-linked with NDGA, while others can be cross-linked with a different agent, such as EDC or other cross-linking agent.

In yet other embodiments, three or more different cross-linking agents may be used to yield synthetic collagen fibers having different properties, including, for example, intra-body degradation time, tensile strength and the like. For example, a first set of cross-linked collagen fibers 11 can be absorbed or resorbed by the body within about a first day (e.g., 1-10 weeks, such as 1-4 weeks) range while a second set of (different) cross-linked fibers can be absorbed or resorbed by the body within a longer day range (e.g., 6-52 weeks, such as between about 10-20 weeks). The collagen fibers 11 of each cross-linked type may have the same diameter or different diameters and collagen fibers of each particular cross-linked type may include fibers of different diameters. If the latter, for example, smaller cross-sectional/diameter NDGA fibers (e.g., about 0.1 mm or less, on average, dry) may have increased strength relative to thicker NDGA-treated fibers (e.g., about 0.15 mm or greater, on average, dry).

In some embodiments, each yarn 10y can be configured with collagen fibers 11, some of which are cross-linked with different cross-linking agents than others. In other embodiments, each yarn 10y can include the same cross-linked fibers (of the same size).

In some embodiments, weft yarns can have the same cross-linked fibers while warp yarns can all have the same but different cross-linked fibers from the weft yarns. In other embodiments, some weft yarns can have a first type of cross-linked fibers while others can have a different type of cross-linked fibers. In some embodiments, some warp yarns can have a first type of cross-linked fibers while others can have a different type of cross-linked fibers. In some embodiments, only one type of warp or weft yarn can have a blend of different cross-linked fibers. In some embodiments, either the weft yarns or the warp yarns can have different cross-linked collagen fibers while the other can be provided with the same type of cross-linked fibers.

FIGS. 9A-9D illustrate yet another embodiment of a ribbon 10 with an integrated suture 20. In this embodiment, the ribbon 10 is formed of 100 percent collagen fibers. That is, the ribbon body 10b and suture 20 are both formed of only elongate lengths of collagen fiber yarns 10y, 20y, each yarn including multiple collagen fibers. The suture yarns 20y are longer than the ribbon body warp yarns 10y, typically at least about 50% longer, so as to extend outward between about 2-20 inches on each end of the ribbon body 10b to form extensions 20e (also referred to as "tails") that can be used for attachment to local soft tissue and/or bone. The suture collagen yarns 20y can be pre-braided fibers and/or pre-braided yarns that are then woven into the ribbon body 10b. The suture yarns 20y can form a single braided warp suture yarn in the ribbon body 10b or, a multiple braided suture yarns in the woven ribbon body 10b. In some embodiments, the suture yarns 20y comprise multiple twisted or braided collagen fibers and define at least two (shown as three) warp yarns of the ribbon body. However, outside the ribbon body, the suture yarns can be braided together to form the extensions or tails 20e.

Figure 10:
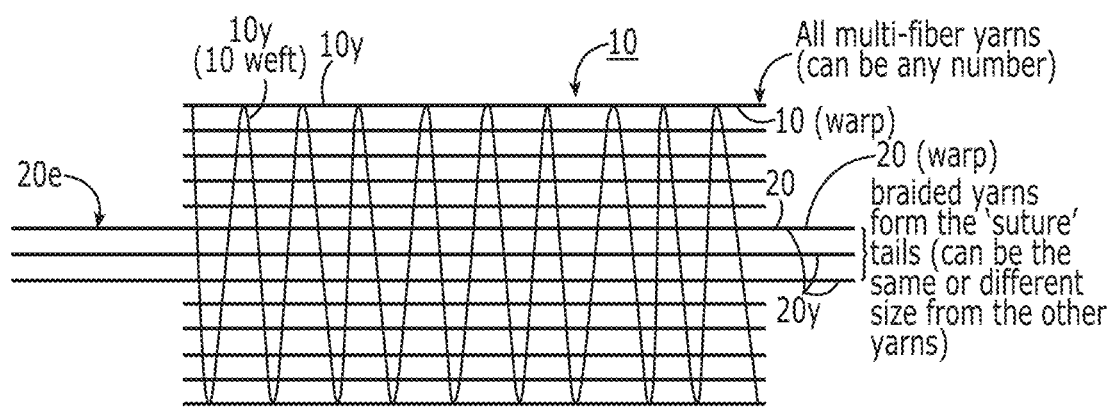
FIG. 10 is a schematic illustration of a flat ribbon with an integrated suture configuration according to embodiments of the present invention.

FIG. 10 illustrates that the suture yarns 20y can comprise a plurality of warp yarns 20warp that define some of the ribbon body warp yarns 10warp and extend along a center of the ribbon body 10b with shorter warp ribbon yarns 10y on each side thereof (shown as five warp yarns on each side of the suture yarns 20y, but less or more may be used). The ribbon body 10b also includes weft yarns 10weft. As shown, there are three braided multi-fiber collagen yarns 20y that form the suture tails 20e and these yarns can be the same or a different size from the ribbon body yarns 10y. Each ribbon body yarn 10y can include a plurality of collagen fibers, typically between about 3-20, and more typically between about 5-10, and in particular embodiments, about 8 long collagen fibers.

Figure 11:
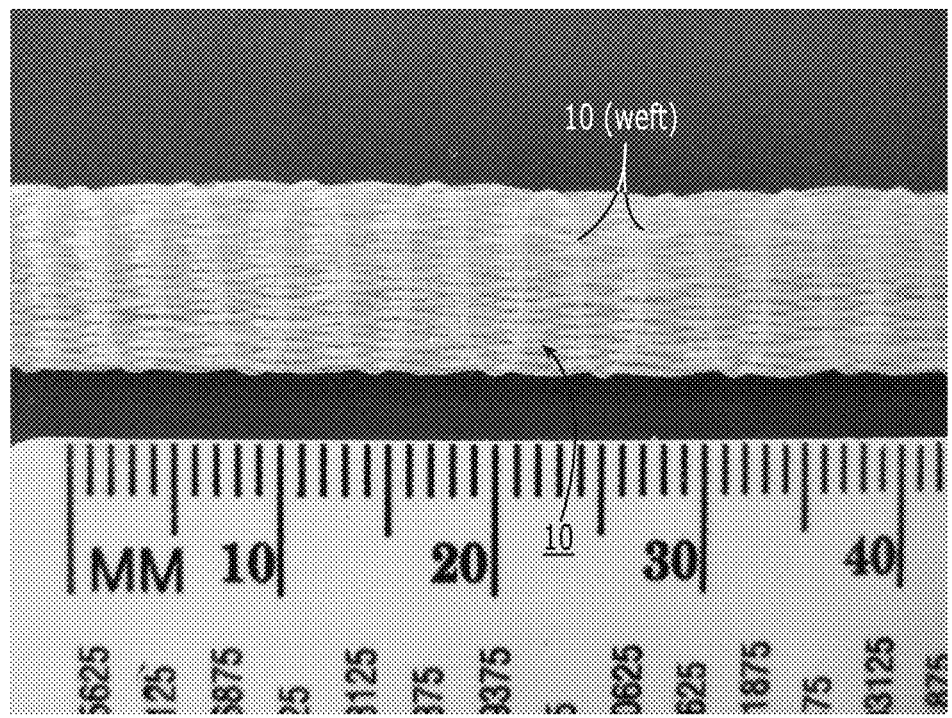
FIG. 11 is a digital photograph of a ribbon (40 warp yarns) made from carbodiimide cross-linked collagen fibers according to some embodiments of the present invention.

FIG. 11 illustrates the ribbon 10 can include one or more (shown as having a sinusoidal shape) weft yarns 10weft that has a frequency, on average, of about 5 mm (from peak to peak or base to base). In this embodiment, there are about 40 warp yarns 10warp and each yarn may have a plurality of fibers (e.g., 4-20 braided fibers per yarn, typically about 8 as shown). In this embodiment, the fibers are all collagen fibers cross-linked with carbodiimide.

Figure 12:
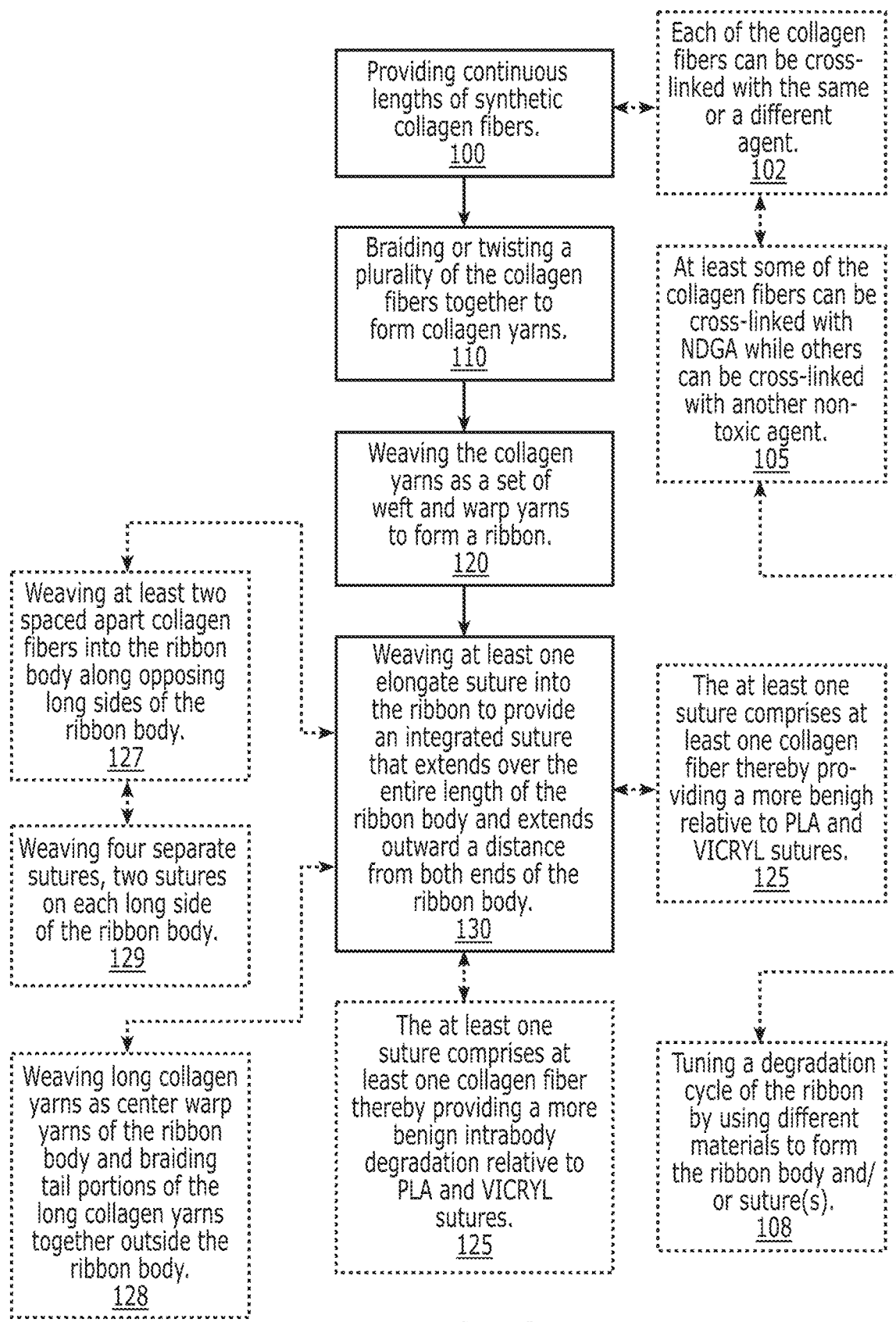
FIG. 12 is a flow chart of exemplary operations that can be used to carry out embodiments of the present invention.

FIG. 12 illustrates some operations that can be used to carry out embodiments of the invention. Continuous lengths of synthetic collagen fibers are provided (block 100). A plurality of the collagen fibers are braided or twisted together to form collagen yarns (block 110). The collagen yarns are woven as a set of weft and warp yarns to form a ribbon (block 120). At least one elongate suture can be woven over ribbon yarns or as warp yarns in the ribbon body to provide (a straight lengthwise oriented) integrated suture that extends over the entire length of the ribbon body and extends outward a distance from both ends of the ribbon body (block 130).

Each of the collagen fibers can be cross-linked with the same or a different agent (block 102), such as NDGA. At least some of the collagen fibers can be cross-linked with NDGA while others can be cross-linked with another non-toxic agent (block 105). The at least one suture can include least one collagen fiber, thereby providing a more benign intrabody degradation relative to PLA and VICRYL sutures (block 125).

In some embodiments, the method can include tuning a degradation cycle of the ribbon by using different materials to form the ribbon body and/or suture(s) (block 108).

The weaving of the at least one suture can be carried out by weaving at least two spaced apart collagen fibers into the ribbon body along opposing long sides of the ribbon body (block 127). In some embodiments, the weaving of the at least one suture can be carried out by weaving four separate sutures (over one primary surface of the ribbon body yarns), two sutures on each long side of the ribbon body (block 129). The weaving can include weaving long collagen yarns as warp yarns of the ribbon body and braiding tail portions of the long collagen yarns together outside the ribbon body (block 128).

Also, the ribbon body and/or suture(s) can optionally be coated, impregnated and/or amalgamated with a gel or other material. The coating may be to promote fibroblasts, and/or comprise one or more of an anti-inflammatory agent, an antibiotic or other therapeutic agent.

The ribbon body 10b and/or sutures(s) 20 are biocompatible and may be absorbed, resorbed and/or biodegradable over time.

The ribbon body can be configured to have similar or greater tensile strength, stiffness and dynamic flexibility as corresponding natural tissue, e.g., natural ligament or tendon fibers. Embodiments of the invention may be particularly suitable for augmenting, repairing or replacing tendons and ligaments.

In some embodiments, the fibers comprise any collagen fibers formed in any suitable manner to be acceptable as a biomedical implant/construct.

In particular embodiments, the fibers can comprise NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products. For additional discussion of the NDGA polymerized fibers, see, Thomas J. Koob, *Biomimetic approaches to Tendon Repair*, Comparative Biochemistry and Physiology Part A 133 (2002) 1171-1192. See also, U.S. Provisional Application Ser. No. 61/422,363, the contents of which are hereby incorporated by reference as if recited in full herein.

Generally stated, to make the collagen fibers, preparatory donor collagen material can be pepsin-derived or solubilized collagen that is processed/purified. The purified collagen preparatory material is dialyzed a plurality of times in a selected liquid for a desired period of time. The dialyzing is typically repeated three times. The dialyzing can be carried out against dionized (DI) water in a volume ratio of between about 30:1 to about 100:1, typically about 60 to 1, for between about 30-90 minutes, typically about 40 minutes. The dialyzing can form a substantially clear gel of collagen fibrils indicating good organization (substantially parallel fibrils), where opacity indicates less organization. The organization can help improve tensile strength of subsequently cross-linked fibers.

The dialyzed collagen material can be incubated for a desired time before placing in a fiber-forming buffer. The dialyzed gel can be cross-linked to provide collagen fibers for medical constructs. The polymerization (e.g., cross-linking) can be carried out using NDGA and the resultant NDGA treated collagen fibers can be relatively thin, such as, for example, about 0.08 mm dry diameter (on average).

The incubation may be for at least about 24 hours, typically 24-48 hours, and may be at room temperature of between about 15-30° C., typically about 25° C. The dialysis process can be used before cross-linking for subsequent use with any suitable cross-linking materials, to promote collagen organization, such as, for example, and the process is not limited to NDGA, but may be useful with other materials, including, for example, glutaraldehyde. For additional discussion of methods used to form high-strength NDGA treated collagen fibers, see, U.S. application Ser. No. 11/964,756, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of making a medical ribbon, comprising:
providing a plurality of fibers, wherein the plurality of fibers are continuous length cross-linked collagen fibers;
forming the plurality of fibers into yarns;
providing at least one suture;
providing the yarns as warp yarns and one or more weft yarns; and
weaving the warp yarns and the one or more weft yarns together to form a ribbon body with a length while crossing the one or more weft yarns over a top of the at least one suture at intervals along the length of the ribbon body to attach the at least one suture to the ribbon body, wherein the at least one suture has at least one tail end that extends a distance of at least about 1 inch off at least one end of the ribbon body, wherein some of the plurality of fibers are cross-linked with a first agent and some of the plurality of fibers are cross-linked with a second agent that is different than the first agent.

2. The method of claim 1, wherein the weaving step is carried out by attaching a single suture as the at least one suture to the ribbon body so that the single suture resides in a substantially straight line proximate a longitudinally extending centerline of the ribbon body, and wherein the single suture is formed of a different material than the plurality of fibers of the yarns.

3. The method of claim 1, wherein the ribbon body comprises first and second long sides laterally spaced apart across a width of the ribbon body, wherein the providing the at least one suture is carried out to provide a plurality of sutures, and wherein the weaving step is carried out to attach the plurality of sutures to the ribbon body so that at least one suture of the plurality of sutures resides in a substantially straight line proximate the first long side of the ribbon body and at least one suture of the plurality of sutures resides in a substantially straight line proximate the second long side of the ribbon body.

4. The method of claim 1, wherein the ribbon body comprises a perimeter with first and second long sides that are laterally spaced apart across a width of the ribbon body, wherein the providing the at least one suture is carried out to provide at least four sutures, and wherein the weaving step attaches at least two of the at least four sutures to be parallel and adjacent each of the first and second long sides of the ribbon body.

5. The method of claim 1, wherein the weaving step is carried out to have the one or more weft yarns hold the at least one suture at discrete repeating segments along the length of the ribbon body.

6. The method of claim 1, wherein the plurality of fibers comprise NDGA-polymerized collagen fibers.

7. The method of claim 1, wherein the first and second agents provide some of the plurality of fibers with a different fiber tensile strength and a different intrabody degradation rate than others of the plurality of fibers.

8. The method of claim 7, wherein the first agent is NDGA and the second agent is 1-ethyl-3-(3-dimethylaminopropyl)-carbodiimide (EDC), and wherein the fibers cross-linked with EDC degrade faster than the fibers cross-linked with NDGA.

9. The method of claim 1, wherein the at least one suture is defined by a plurality of long warp yarns with a length that is at least about 50% greater than others of the warp yarns in the ribbon body, wherein the plurality of long warp yarns are woven medially to be proximate a longitudinally extending centerline of the ribbon body, and wherein the plurality of long warp yarns extend a distance off each opposing end of the ribbon body forming two opposing tail ends as the at least one tail end.

10. The method of claim 1, wherein the at least one suture comprises at least four separate sutures, wherein the at least four separate sutures include two parallel sutures attached to and extending along the length on one side of a longitudinally extending centerline of the ribbon body and the at least four separate sutures further include two parallel sutures attached to and extending along the length on an opposing side of the longitudinally extending centerline of the ribbon body.

11. The method of claim 1, wherein the at least one suture comprises at least one nordihydroguaiaretic acid (NDGA) treated or at least one carbodiimide cross-linked collagen fiber.

12. The method of claim 1, wherein the at least one suture comprises by a plurality of yarns comprising cross-linked synthetic collagen fibers, wherein the at least one suture extends only longitudinally along the length of the ribbon body and has a length sufficient to extend outwardly therefrom to define tail ends as the at least one tail end, and wherein the tail ends have a length in a range of about 2 inches to about 15 inches.

13. The method of claim 1, wherein the plurality of fibers comprise carbodiimide cross-linked collagen fibers.

14. The method of claim 1, wherein the at least one suture comprises a plurality of elongate synthetic collagen fibers.

15. The method of claim 1, wherein some of the plurality of fibers forming one or more of the warp yarns are cross-linked with the first agent while others of the plurality of fibers forming the one or more warp yarns are cross-linked with the second agent.

16. The method of claim 1, wherein the plurality of fibers forming one or more of the warp yarns are cross-linked with the first agent while the plurality of fibers forming another one or more of the warp yarns are cross-linked with the second agent.

17. A method of making a medical ribbon, comprising:
providing a plurality of yarns comprising fibers, wherein the fibers are continuous length cross-linked collagen fibers, wherein the provided plurality of yarns are provided as warp yarns and one or more weft yarns;
providing at least one suture; and
weaving the warp yarns and the one or more weft yarns together to form a ribbon body with a length while crossing the one or more weft yarns over a top of the at least one suture at intervals along the length of the ribbon body to attach the at least one suture to the ribbon body so that the at least one suture has at least one tail end that extends a distance of at least about 1 inch off at least one end of the ribbon body,
wherein the ribbon body has first and second primary surfaces and a perimeter with first and second long sides and first and second short sides, wherein the at least one suture extends in a straight linear orientation along the length of the ribbon body, wherein the at least one suture extends a length beyond both the first and second short sides of the ribbon body forming two tail ends as the at least one tail end, wherein the at least one suture is held under the one or more weft yarns with the at least one suture visible on only one of the first primary surface or the second primary surface of the ribbon body, wherein the one or more weft yarn terminates at the first and second short sides of the ribbon body, and wherein the at least one suture is spaced laterally inward from an outer edge of the first and second long sides of the ribbon body and extends out from the first and second short sides of the ribbon body while other adjacent warp yarns closer to the outer edge of the first and second long sides of the ribbon body terminate at the first and second short sides of the ribbon body.

18. A method of making a medical ribbon, comprising:
providing a plurality of warp yarns having a first length, each warp yarn comprising a plurality of synthetic collagen fibers;
providing a plurality of long warp yarns having a second length that is at least about 50% longer than the plurality of the warp yarns having the first length, each long warp yarn comprising a plurality of synthetic collagen fibers;
providing a plurality of weft yarns, each weft yarn comprising a plurality of synthetic collagen fibers; and
weaving the weft yarns and the warp yarns having the first and second lengths together to form a ribbon body, with the long warp yarns extending beyond ends of the ribbon body a distance of at least about 1 inch to define tails, wherein the plurality of synthetic collagen fibers forming one or more of the warp yarns are cross-linked with a first agent while the plurality of synthetic collagen fibers forming another one or more of the warp yarns are cross-linked with a second agent different from the first agent.

19. The method of claim 18, wherein the weaving step is carried out using the long warp yarns as substantially central warp yarns of the ribbon body with the warp yarns of the first length on both sides thereof.

20. The method of claim 18, further comprising braiding loose end segments of the long warp yarns that extend beyond at least one end of the ribbon body to define a braided tail.

21. A method of making a medical ribbon, comprising:
providing a plurality of warp yarns and at least one weft yarn, wherein the plurality of warp yarns and the at least one weft yarn comprise cross-linked synthetic collagen fibers;
providing at least one suture, wherein the at least one suture is of a different material than the provided plurality of warp yarns and the at least one weft yarn; and
weaving the plurality of warp yarns and the at least one weft yarn together to form a ribbon body with a length while crossing the at least one weft yarn over a top of the at least one suture at intervals along the length of the ribbon body to attach the at least one suture to the ribbon body, wherein the at least one suture has opposing tail ends that extend a distance of about 1-15 inches off a respective end of the ribbon body, wherein some of the synthetic collagen fibers are cross-linked with a first agent while others of the synthetic collagen fibers are cross-linked with a second agent different from the first agent.

22. The method of claim 21, wherein the synthetic collagen fibers of at least one of the plurality of warp yarns are cross-linked with the first agent while the synthetic collagen fibers of at least another one of the plurality of warp yarns are cross-linked with the second agent.

23. The method of claim 21, wherein the ribbon body has a perimeter with first and second long sides and first and second short sides, the short sides defining longitudinally opposing ends of the ribbon body, wherein the at least one weft yarn terminates at each of the first and second short sides of the ribbon body, and wherein the at least one suture is spaced laterally inward from an outer edge of the first and second long sides of the ribbon body and extends out from the ribbon body while adjacent warp yarns of the plurality of warp yarns that are closer to the first and second long sides of the ribbon body terminate at the longitudinally opposing ends of the ribbon body.

24. The method of claim 21, wherein the at least one suture has a length that is at least 50% longer than the plurality of warp yarns of the ribbon body.

25. The method of claim 21, wherein the ribbon body has first and second primary surfaces and a perimeter with first and second long sides and first and second short sides, wherein the at least one suture extends in a straight linear orientation along the length of the ribbon body, wherein the at least one suture extends a length beyond both the first and second short sides of the ribbon body forming two tail ends, wherein the at least one suture is held under the at least one weft yarn with the at least one suture visible on only one of the first primary surface or the second primary surface of the ribbon body, wherein the at least one weft yarn terminates at the first and second short sides of the ribbon body, and wherein the at least one suture is spaced laterally inward from an outer edge of the first and second long sides of the ribbon body and extends out from the first and second short sides of the ribbon body while warp yarns closer to the outer edge of the first and second long sides of the ribbon body terminate at the first and second short sides of the ribbon body.

26. The method of claim 21, the method further comprising selecting a warp yarn for the provided plurality of warp yarns and/or selecting a weft yarn for the provided at least one weft yarn to provide tunable degradation thereby allowing different segments of the ribbon body to degrade at different rates corresponding to a target treatment of a patient.

* * * * *

UNITED STATES PATENT AND TRADEMARK OFFICE
CERTIFICATE OF CORRECTION

PATENT NO. : 10,653,514 B2
APPLICATION NO. : 15/466299
DATED : May 19, 2020
INVENTOR(S) : Koob et al.

Page 1 of 1

It is certified that error appears in the above-identified patent and that said Letters Patent is hereby corrected as shown below:

In the Claims

Column 13, Line 61, Claim 12:
Please correct "comprises by a" to read -- comprises a --

Signed and Sealed this
Sixth Day of October, 2020

Andrei Iancu
*Director of the United States Patent and Trademark Office*